United States Patent [19]

Bruderer et al.

[11] 4,336,268
[45] Jun. 22, 1982

[54] CYCLOHEXENE DERIVATIVE ANALGESICS

[75] Inventors: Hans Bruderer, Benken; Albert E. Fischli, Riehen; Rudolf Pfister, Basel, all of Switzerland

[73] Assignee: Hoffmann-La Roche Inc., Nutley, N.J.

[21] Appl. No.: 228,793

[22] Filed: Jan. 27, 1981

[30] Foreign Application Priority Data

Jan. 29, 1980 [CH] Switzerland .......................... 724/80

[51] Int. Cl.³ .......................................... A61K 31/135
[52] U.S. Cl. ..................... 424/330; 564/338; 564/171; 560/27; 568/647; 568/442; 548/452
[58] Field of Search ....................... 564/305, 336, 338; 424/330

[56] References Cited

U.S. PATENT DOCUMENTS

| | | | |
|---|---|---|---|
| 2,647,122 | 7/1953 | Archer et al. | 564/336 X |
| 3,109,845 | 11/1963 | Seeger et al. | 424/199 X |
| 3,405,139 | 10/1968 | Haack et al. | 564/338 X |
| 3,408,396 | 10/1968 | Suh et al. | 564/336 X |
| 3,485,873 | 12/1969 | Aceto et al. | 564/336 |
| 4,269,788 | 5/1981 | Muller et al. | 260/501.1 |

OTHER PUBLICATIONS

Psotta et al., Tetrahedron, vol. 35, (1979), 255–257.
Schwenker et al., Archiv. der Pharmazie, vol. 301, (1968), 592–595.

Primary Examiner—Bernard Helfin
Attorney, Agent, or Firm—Jon S. Saxe; Bernard S. Leon; William G. Isgro

[57] ABSTRACT

Cyclohexenes of the formula

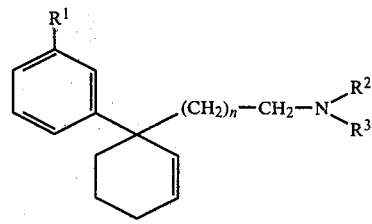

wherein $R^1$ is hydroxy or lower alkoxy; n is 1 or 2; $R^2$ is lower alkyl; and $R^3$ is hydrogen, lower alkyl, lower alkenyl or lower cycloalkylmethyl, and their pharmaceutically acceptable acid addition salts are disclosed. The compounds of formula I have analgesic activity and are useful for the control of pains.

9 Claims, No Drawings

CYCLOHEXENE DERIVATIVE ANALGESICS

BRIEF SUMMARY OF THE INVENTION

The invention relates to compounds of the formula

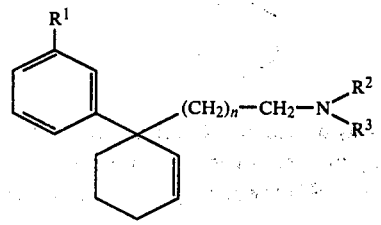

I wherein $R^1$ is hydroxy or lower alkoxy; n is the integer 1 or 2; $R^2$ is lower alkyl; and $R^3$ is hydrogen, lower alkyl, lower alkenyl or lower cycloalkylmethyl, and their pharmaceutically acceptable acid addition salts.

In another aspect, the invention relates to intermediates of the formulae

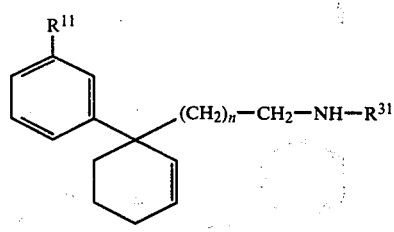

II wherein $R^{11}$ is lower alkoxy; $R^{31}$ is hydrogen, lower alkenyl, or lower cycloalkylmethyl; n is the integer 1 or 2;

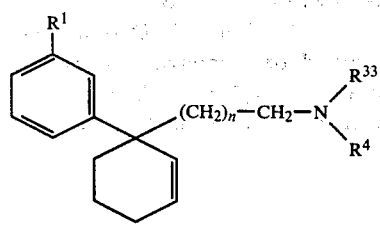

III wherein $R^1$ and n are as previously described; $R^{33}$ is hydrogen, lower alkyl, lower alkenyl or lower cycloalkylmethyl and $R^4$ is formyl, lower alkanoyl or lower alkoxycarbonyl; or $R^{33}$ is lower alkyl and $R^4$ is lower cycloalkylcarbonyl;

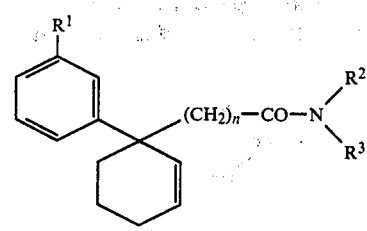

IV wherein n, $R^1$, $R^2$ and $R^3$ are as previously described;

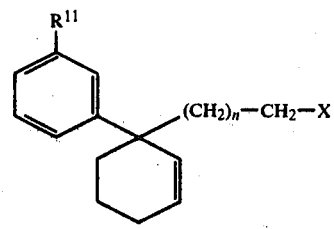

V wherein $R^{11}$ is lower alkoxy; n is the integer 1 or 2; and X is a leaving group;

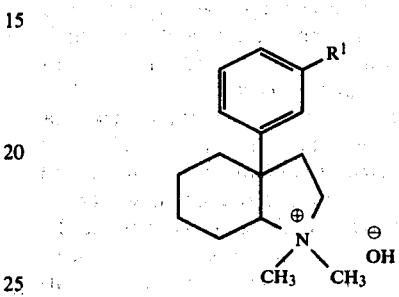

VII wherein $R^1$ is as previously described, and its corresponding quaternary ammonium salt;

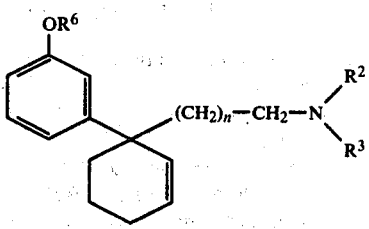

VIII wherein n, $R^2$ and $R^3$ are as previously described and $R^6$ is a protecting group; and

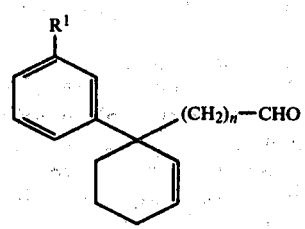

IX wherein $R^1$ and n are as previously described.

In a further aspect, the invention relates to a process for preparing the compounds of formula I.

In still another aspect, the invention relates to a method of using the compounds of formula I in the control of pain.

DETAILED DESCRIPTION OF THE INVENTION

The invention relates to cyclohexene derivatives. More particularly, the invention is concerned with 1-phenyl-2-cyclohexene-1-alkylamine derivatives.

The cyclohexene derivatives of the invention are compounds characterized by the formula

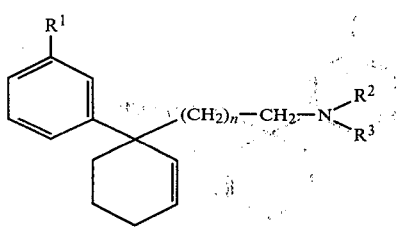

wherein $R^1$ is hydroxy or lower alkoxy; n is the integer 1 or 2; $R^2$ is lower alkyl; and $R^3$ is hydrogen, lower alkyl, lower alkenyl or lower cycloalkylmethyl, and their pharmaceutically acceptable acid addition salts.

The aforementioned compounds and salts possess valuable pharmacodynamic properties.

Objects of the present invention are the compounds of formula I and their pharmaceutically acceptable acid addition salts; the preparation of these derivatives and the intermediates for the preparation of these derivatives; medicaments containing these derivatives and the manufacture of such medicaments, as well as the use of these derivatives in the control or prevention of illnesses.

The compounds of formula I contain an asymmetric carbon atom and, accordingly, the invention relates to not only the optically uniform enantiomeric forms of these compounds but also mixtures thereof, such as the racemates.

Preferred among the compounds of formula I are those wherein $R^1$ is hydroxy or methoxy, $R^2$ and $R^3$ each signify a lower alkyl group (especially a methyl group), and n stands for 1.

A particularly preferred compound of formula I is 1-(m-methoxyphenyl)-N,N-dimethyl-2-cyclohexene-1-ethylamine; this is true not only for the two optically uniform enantiomeric forms of this compound but also for mixtures thereof, including the racemate, which is especially preferred in the scope of the invention.

Another preferred compound of formula I is 1-(m-hydroxyphenyl)-N,N-dimethyl-2-cyclohexene-1-ethylamine.

Examples of other compounds of formula I are 1-(m-methoxyphenyl)-N,N-dimethyl-2-cyclohexene-1-propylamine, 1-(m-methoxyphenyl)-N-methyl-2-cyclohexene-1-ethylamine, N-allyl-1-(m-methoxyphenyl)-N-methyl-2-cyclohexene-1-ethylamine and N-cyclopropylmethyl-1-(m-methoxyphenyl)-N-methyl-2-cyclohexene-1-ethylamine.

According to the process provided by the invention, the cyclohexene derivatives of the invention, that is, the compounds of formula I and their pharmaceutically acceptable acid addition salts, are prepared by (a) appropriately substituting a compound of the formula

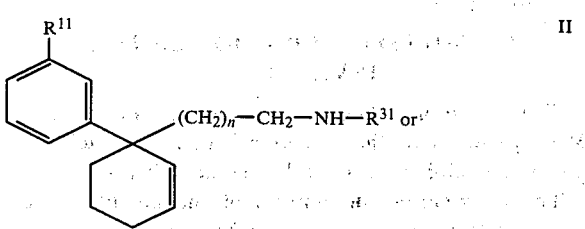

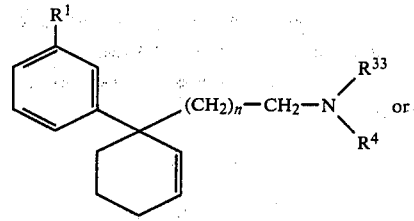

wherein n is as previously described, $R^{11}$ is lower alkoxy, $R^{31}$ is hydrogen, lower alkenyl or lower cycloalkylmethyl, and $R^{32}$ is lower alkyl, at the nitrogen atom, or (b) reducing a compound of the formula

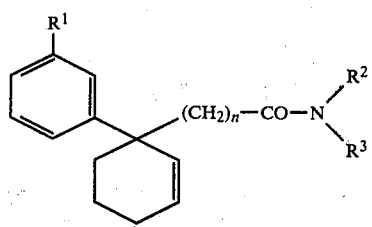

wherein $R^1$, $R^2$, $R^3$ and n are as previously described and either $R^{33}$ is hydrogen, lower alkyl, lower alkenyl or lower cycloalkylmethyl and $R^4$ is formyl, lower alkanoyl or lower alkoxycarbonyl, or $R^{33}$ is lower alkyl and $R^4$ is lower cycloalkylcarbonyl, or (c) reacting a compound of the formula

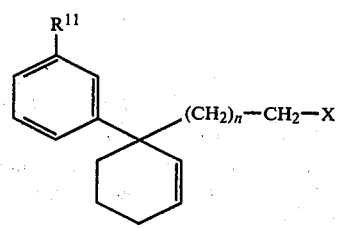

wherein $R^{11}$ and n are as previously described and X is a leaving group, with an amine of the formula $$HN\begin{matrix}R^2\\R^3\end{matrix} \qquad VI$$

wherein $R^2$ and $R^3$ are as previously described, or (d) heating a quaternary ammonium base of the formula

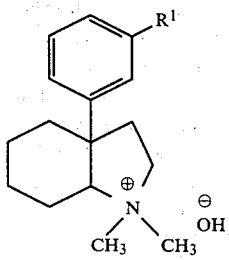

VII wherein $R^1$ is as previously described, or subjecting a suitable corresponding quaternary ammonium salt to heating or treatment with a base, or (e) cleaving off the alkyl group denoted by $R^5$ or the protecting group denoted by $R^6$ from a compound of the formula

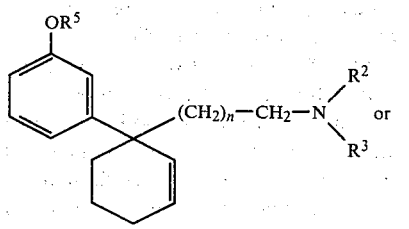

Ib

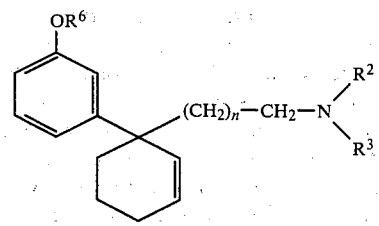

VIII wherein $R^2$, $R^3$ and n are as previously described, and $R^5$ is lower alkyl and $R^6$ is a protecting group, or (f) etherifying a compound of the formula

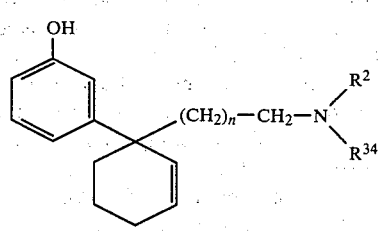

Ic wherein n and $R^2$ are as previously described, and $R^{34}$ is lower alkyl, lower alkenyl or lower cycloalkylmethyl, or (g) reacting a compound of the formula

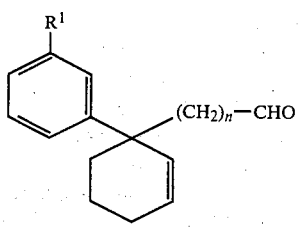

IX wherein $R^1$ and n are as previously described, under reducing conditions with an amine of the formula VI hereinbefore, or (h) resolving a racemic compound of formula I into its optically active antipodes, or (i) converting a compound of formula I into a pharmaceutically acceptable acid addition salt.

As used herein, the term "lower alkyl" denotes straight-chain or branched-chain saturated hydrocarbon groups containing at most 4 carbon atoms, for example, methyl and the like. The term "lower alkoxy", alone or in term "lower alkoxycarbonyl", denotes a lower alkyloxy group in which the lower alkyl moiety is as described above. The term "lower alkenyl" denotes straight-chain or branched-chain hydrocarbon groups which contain 3–5 carbon atoms and one olefinic double bond, for example, allyl and the like. The term "lower alkanoyl" denotes acyl groups derived from straight-chain or branched-chain alkanecarboxylic acids containing 2–4 carbon atoms, for example, acetyl and the like. The terms "lower cycloalkylmethyl" and "lower cycloalkylcarbonyl" denote groups containing a total of at most 5 carbon atoms, for example, cyclopropylmethyl, cyclopropylcarbonyl and the like.

The N-substitution of the compounds of formula II or Ia is carried out according to known methods. For example, the N-substitution can be carried out using a halide or dialkyl sulfate corresponding to the group to be introduced. However, the N-substitution is preferably carried out reductively; for example, using an aldehyde corresponding to the group to be introduced in the presence of formic acid or by reaction with an aldehyde corresponding to the group to be introduced and subsequent treatment with a suitable reducing agent, such as, sodium cyanoborohydride, sodium borohydride or the like.

Thus, for example, by reacting a compound of formula Ia, wherein $R^{32}$ is methyl, with allyl bromide, there is obtained a corresponding compound of formula I wherein $R^2$ is methyl and $R^3$ is allyl. When formaldehyde and formic acid are used, a compound of formula II wherein $R^{31}$ is hydrogen or a compound of formula Ia wherein $R^{32}$ is methyl yields a corresponding compound of formula I wherein $R^2$ and $R^3$ each signify methyl, and a compound of formula II wherein $R^{31}$ is cyclopropylmethyl yields a corresponding compound of formula I wherein $R^2$ is methyl and $R^3$ is cyclopropylmethyl.

The process parameters for the carrying out of the various embodiments of the N-substitution of compounds of formulas II and Ia are known to any person of ordinary skill in the art. It will, of course, be appreciated that only those methods are used which selectively give the desired N-substitution, and it will be appreciated in particular that in the case of reductive methods there can be used only those which do not affect the olefinic double bond in the cyclohexene part of the molecule.

The reduction of the compounds of formula III or IV is carried out according to known methods. It will, of course, be appreciated that the method used must be one which leads selectively to the desired compounds of formula I, and it will be appreciated in particular that the olefinic double bond in the cyclohexene part of the molecule must not be affected. The reduction is conveniently carried out using a very reactive complex hydride, such as, lithium aluminum hydride or diisobutyl aluminum hydride in the presence of a suitable inert organic solvent, such as ether, tetrahydrofuran, monoglyme, diglyme or the like.

The leaving group denoted by symbol X in formula V can be halogen, especially chlorine, bromine or iodine, or an equivalent leaving group, for example, an arylsulfonyloxy group, such as, tosyloxy; an alkylsulfonyloxy group, such as mesyloxy, and the like. The process parameters for the reaction of a compound of formula V with an amine of formula VI are familiar to any person skilled in the art. The reaction is conveniently carried out in the presence of a suitable inert organic solvent, for example, an alcohol, such as, methanol, ethanol or the like, dimethylformamide, toluene, benzene, xylene, monoglyme, diglyme or the like, in the presence of an acid-binding agent, for example, an inorganic base, such as, sodium carbonate, potassium carbonate or the like, a tertiary amine, such as, triethylamine, N-ethyldiisopropylamine, quinuclidine, pyridine or the like. Moreover, an excess of the amine of formula VI can be used and can thereby serve as the acid-binding agent.

The heating of a quaternary ammonium base of formula VII or a suitable corresponding quaternary salt or the treatment of such a salt with a base brings about the cleavage of the 5-membered heterocyclic ring and the introduction of a double bond in the 6-membered alicyclic ring, there being obtained a corresponding compound of formula I wherein n is the integer 1 and each of $R^2$ and $R^3$ is methyl.

If a quaternary ammonium base of formula VII is used as the starting material, then this base is conveniently heated in the absence of a solvent at a temperature in the range of from about 100° to 200° C., preferably in the range of from about 160° to 180° C., the corresponding amine of formula I which is formed is removed by distillation in a high vacuum.

The fluorides are the especially suitable quaternary ammonium salts corresponding to the quaternary ammonium bases of formula VII. Such fluorides are converted into corresponding compounds of formula I conveniently by heating them in a suitable solvent, such as, acetonitrile or the like, for about 1 hour, preferably at about the reflux temperature of the chosen solvent, or by treating them in a suitable solvent with a suitable base, for example, with sodium tert.amylate in a mixture of tert.butanol and toluene or the like, the treatment conveniently is carried out at room temperature.

The cleavage of the lower alkyl denoted by $R^5$ in the compounds of formula Ib is carried out using methods which are known to any person of ordinary skill in the art for the carrying out of such an ether cleavage. For the ether cleavage, there are conveniently used acidic reagents, such as, boron tribromide in a suitable inert organic solvent, for example, a halogenated hydrocarbon, such as, methylene chloride, chloroform, or the like; hydrobromic acid; pyridine hydrochloride, or the like.

Suitable protecting groups denoted by $R^6$ in the compounds of formula VIII are, of course, only those which can be cleaved using methods which selectively remove these protecting groups without affecting other structural elements present in the molecule. Examples of such protecting groups are readily cleavable metal-organic groups, preferably, trialkylsilyl groups, such as, trimethylsilyl, and the like, readily cleavable acetal and ketal protecting groups, such as, tetrahydropyran-2-yl and the like. The removal of the protecting group from the compounds of formula VIII is carried out according to known methods. When choosing the method, the nature of the protecting group to be removed must, of course, be taken into consideration and, moreover, care must be taken that only the protecting group is selectively removed and that other structural elements present in the molecule are not affected. Thus, for example, the trimethylsilyl group can be cleaved by treatment with dilute hydrochloric acid in tetrahydrofuran or the like and the tetrahydropyran-2-yl group can be cleaved under mild acidic aqueous conditions, for example, using 0.1 N hydrochloric acid.

The etherification of a compound of formula Ic is carried out according to known methods which are familiar to any person of ordinary skill in the art. It will, of course, be appreciated that the method used must be one which selectively alkylates the phenolic hydroxyl group without affecting other structural elements present in the molecule. The etherification is conveniently carried out using a diazoalkane, such as, diazomethane in a suitable inert organic solvent, for example, an ether, such as, diethyl ether, tetrahydrofuran, dioxane, or the like, at a temperature in the range of from about 0° C. up to about 50° C., preferably at about room temperature.

Methods for the reaction of a compound of formula IX with an amine of formula VI, which reaction is carried out under reducing conditions, are familiar to any person of ordinary skill in the art. Of course, it will be appreciated that there can be used only those methods which do not bring about a reduction of the olefinic double bond present in the cyclohexene moiety of the compounds of formula IX or of the reducible groups which may be present in the amines of formula VI. A borohydride, such as, sodium cyanoborohydride, sodium borohydride or the like can be used as the reducing agent. The reaction is conveniently carried out in the presence of a suitable inert organic solvent, for example, a lower alkanol, such as, methanol, ethanol, isopropanol, or the like.

The resolution of a racemic compound of formula I into the two optically uniform enantiomeric components is carried out according to known methods, conveniently by reaction with an optically active acid, such as, (+)-di-O,O'-p-toluoyl-D-tartaric acid and subsequent separation of the thus-obtained diastereoisomeric salts, for example, by fractional crystallization, from which the optically uniform compounds of formula I can be liberated using a base.

The conversion of compounds of formula I into pharmaceutically acceptable acid addition salts is carried out according to generally known and usual methods. The salts can be formed with inorganic acids and also with organic acids. Examples of such salts are hydrochlorides, hydrobromides, sulfates, methanesulfonates, paratoluenesulfonates, oxalates, tartrates, citrates, maleates, ascorbates, acetates, or the like.

As mentioned earlier, the invention also includes within its scope intermediates for the preparation of the cyclohexene derivatives of formula I, these intermediates are compounds of formulas II, III, IV, V, VII, VIII and IX, hereinbefore. The preparation of such intermediates will now be described, firstly with reference to the Reaction Scheme which follows wherein n and X are as previously described and $R^7$ is lower alkoxy or a protected hydroxy group.

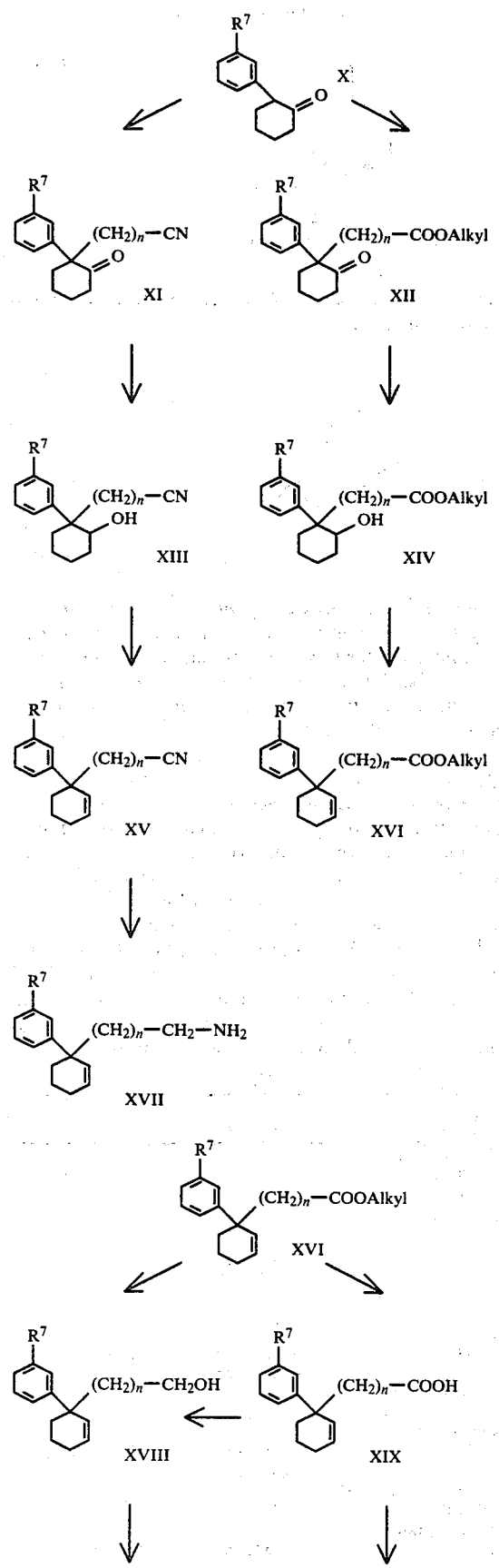

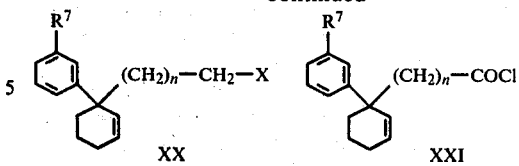

The compounds of formula X, such as, 2-(m-methoxyphenyl)-cyclohexanone are known or can be prepared according to known methods and familiar to any person of ordinary skill in the art. Compounds of formulas XI and XII are obtained from the compounds of formula X by reaction with chloroacetonitrile, β-chloropropionitrile, acrylonitrile, or the like, or ethyl bromoacetate, ethyl β-propionate, ethyl acrylate or the like, in the presence of a strong base. Compounds of formula XIII or XIV are obtained from the compounds of formula XI or XII by reduction. The reduction of the compounds of formula XI conveniently is carried out using sodium borohydride or the like. The reduction of the compounds of formula XII conveniently is carried out by catalytic hydrogenation, for example, over platinum. Compounds of formulas XV and XVI are obtained from the compounds of formula XIII or XIV, for example, by treatment with phosphorus oxychloride in pyridine or by reaction with methanesulfonyl chloride and treatment of the product obtained with potassium acetate in hexamethylphosphoric acid triamide or the like. Compounds of formulas XVII and XVIII are obtained from the compounds of formula XV, XVI or XIX, conveniently by reduction with a reactive complex hydride, such as, lithium aluminum hydride, diisobutyl aluminum hydride or the like. Compounds of formula XIX are obtained from the compounds of formula XVI by alkaline hydrolysis, for example, using potassium hydroxide in ethanol/water. Compounds of formula XX are obtained from the compounds of formula XVIII by replacing the hydroxy group by a leaving group according to known methods, for example, using thionyl chloride, tosyl chloride, mesyl chloride or the like. Compounds of formula XXI are obtained from compounds of formula XIX according to known methods, for example, using oxalyl chloride, thionyl chloride or the like.

Compounds of formula XVII wherein $R^7$ is lower alkoxy are identical with compounds of formula II wherein $R^{31}$ is hydrogen. The remaining compounds of formula II, as well as those of formula Ia, are obtained from the compounds of formula XVII wherein $R^7$ is lower alkoxy by appropriate N-substitution. The introduction of a lower alkyl or lower cycloalkylmethyl group conveniently is carried out by firstly preparing a corresponding formyl, alkoxycarbonyl, alkanoyl or cycloalkylcarbonyl compound and subsequently reducing the resulting compound with a complex hydride, such as, lithium aluminum hydride, diisobutyl aluminum hydride or the like.

Compounds of formula II and Ia can also be prepared by reacting compounds of formula XX wherein $R^7$ is lower alkoxy with ammonia or a corresponding amine, or by reacting compounds of formula XXI wherein $R^7$ is lower alkoxy with ammonia or a corresponding primary amine and reducing the resulting compound with a complex hydride, such as, lithium aluminum hydride, diisobutyl aluminum hydride or the like.

Compounds of formula III are obtained from compounds of formula XVII by appropriate monosubstitution or disubstitution at the nitrogen atom according to known methods and familiar to any person of ordinary skill in the art, whereupon an oxygen protecting group which may be present is cleaved.

Compounds of formula IV are obtained from compounds of formula XXI by reaction with an amine of formula VI according to known methods and familiar to any person of ordinary skill in the art, whereupon an oxygen protecting group which may be present is cleaved.

Compounds of formula XX wherein $R^7$ is lower alkoxy are identical with the compounds of formula V.

Compounds of formula VIII are obtained from compounds of formula XVII wherein $R^7$ is a protected hydroxy group by appropriate monosubstitution or disubstitution at the nitrogen atom according to known methods and familiar to any person of ordinary skill in the art. Compounds of formula VIII can also be obtained by reacting compounds of formula XX wherein $R^7$ is a protected hydroxy group with an amine of formula VI or by reacting a compound of formula XXI wherein $R^7$ is a protected hydroxy group with an amine of formula VI and subsequently reducing the resulting compound with a complex hydride, such as, lithium aluminum hydride, diisobutyl aluminum hydride or the like.

Compounds of formula IX are obtained by oxidizing compounds of formula XVIII, conveniently by means of sulfur trioxide/pyridine complex in dimethyl sulfoxide, oxalyl chloride in dimethyl sulfoxide or other suitable reagents, and subsequently cleaving off an oxygen protecting group which may be present.

For the preparation of quaternary ammonium bases of formula VII or of suitable corresponding quaternary ammonium salts, compounds of formula XI wherein n is the integer 1 are firstly reductively cyclized to give compounds of the formula

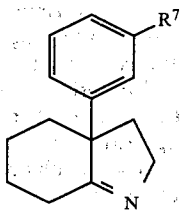

XXII wherein $R^7$ is as previously described, this reductive cyclization conveniently is carried out by catalytic hydrogenation, for example, over palladium. Thereupon, the carbon-nitrogen double bond is reduced, conveniently with sodium borohydride, sodium cyanoborohydride or the like, whereupon the compound obtained is converted into the corresponding quaternary dimethylammonium hydroxide or dimethylammonium salt according to known methods and familiar to any person of ordinary skill in the art, conveniently by monomethylation using formaldehyde and formic acid, subsequent quaternization with methyl iodide and finally replacement of the iodide ion by the desired anion, preferably carried out using a suitable anion exchanger. An oxygen protecting group which may be present can be cleaved at a convenient stage in the synthesis of the quaternary dimethylammonium base or of the quaternary dimethylammonium salt.

Compounds of formula IV wherein n is the integer 1 and each of $R^2$ and $R^3$ is lower alkyl can be obtained not only in the manner described earlier from corresponding compounds of formulas XXI and VI, but also by reducing a compound of the formula

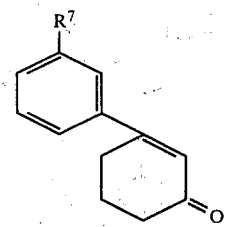

XXIII wherein $R^7$ is as previously described, to give a compound of the formula

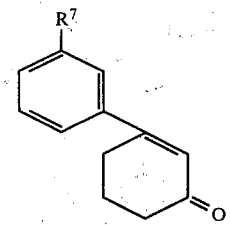

XXIV wherein $R^7$ is as previously described, conveniently using sodium borohydride, sodium cyanoborohydride or the like, and heating the thus-obtained compound of formula XXIV with a corresponding N,N-dialkylacetamide dialkyl acetal, such as, N,N-dimethylacetamide dimethyl acetal, whereupon, an oxygen protecting group which may be present is then cleaved.

The compounds of formula XXIII hereinbefore are known or can be prepared according to known methods and familiar to any person of ordinary skill in the art.

As mentioned earlier, the cyclohexene derivatives of formula I of the invention possess valuable pharmacodynamic properties. As can be demonstrated in the known "writing test", they have analgesic activity. In the Table which follows are compiled the $ED_{50}$ values obtained in this test with representative compounds of formula I. The Table also contains data relating to the acute toxicity of the compounds, that is, $LD_{50}$ in mg/kg in the case of single oral administration to mice.

TABLE

| Compound | $ED_{50}$ in the "writhing test" | $LD_{50}$ |
|---|---|---|
| rac. 1-(m-Methoxyphenyl)-N,N-dimethyl-2-cyclohexene-1-ethylamine hydrochloride | 33 mg/kg p.o. (after 30 min.) 35 mg/kg p.o. (after 60 min.) | 150–300 mg/kg |
| (+)-1-(m-Methoxyphenyl)-N,N-dimethyl-2-cyclohexene-1-ethylamine hydrochloride | 24 mg/kg p.o. (after 60 min.) | 250–500 mg/kg |
| (−)-1-(m-Methoxyphenyl)-N,N-dimethyl-2-cyclohexene-1-ethylamine hydrochloride | 19 mg/kg p.o. (after 60 min.) | 250–500 mg/kg |
| rac. 1-(m-Hydroxyphenyl)-N,N-dimethyl-2-cyclohexene-1-ethylamine hydrochloride | 41 mg/kg p.o. (after 30 min.) 26 mg/kg p.o. | 250–500 mg/kg |

TABLE-continued

| Compound | ED$_{50}$ in the "writhing test" (after 60 min.) | LD$_{50}$ |
| --- | --- | --- |

The strength of activity of the foregoing compounds corresponds to that of codeine and propoxyphene. In comparison with codeine and propoxyphene, they are, however, distinguished by having less undesirable side-effects, especially by less or missing addiction liability.

As mentioned earlier, the compounds of formula I and their pharmaceutically acceptable acid addition salts can be used in the control or prevention of illnesses, especially in the control of pain. The dosage of the compounds of formula I and their pharmaceutically acceptable acid addition salts can vary within wide limits and is, of course, fitted to the individual requirements in any particular case. In the case of oral administration a single dosage of 100–300 mg and a daily dosage of 400–1200 mg can generally be appropriate.

As also mentioned earlier, medicaments containing a compound of formula I or a pharmaceutically acceptable acid addition salt thereof are also an object of the invention as is a process for the preparation of such medicaments, which process comprises bringing one or more compounds of formula I or pharmaceutically acceptable acid addition salts thereof and, if desired, one or more other therapeutically valuable substances into a galenical administration form.

The compounds of formula I and their pharmaceutically acceptable acid addition salts can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions. They can, however, also be administered rectally, for example, in the form of suppositories, locally or percutaneously, for example, in the form of salves, creams, gels or solutions, or parenterally, for example, in the form of injection solutions.

To prepare tablets, coated tablets, dragees and hard gelatin capsules, the compounds of formula I and their pharmaceutically acceptable acid addition salts can be processed with pharmaceutical inert, inorganic or organic excipients. Examples of excipients which can be used for tablets, dragees and hard gelatin capsules are lactose, maize starch or derivatives thereof, talc stearic acid or salts thereof and the like.

Suitable excipients for soft gelatin capsules are, for example, vegetable oils, waxes, fats, semi-solid and liquid polyols and the like. Depending on the nature of the active ingredient, no excipients are, however, generally required to the case of soft gelatin capsules.

Suitable excipients for the preparation of solutions and syrups are, for example, water, polyols, saccharose, glucose and the like.

Suitable excipents for injection solutions are, for example, water, alcohols, polyols, glycerine, vegetable oils and the like.

Suitable excipients for suppositories or for local or percutaneous administration forms are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain therapeutically valuable substances other than the cyclohexene derivatives of formula I provided by the invention.

The Examples which follow further illustrate the invention. All temperatures are in degrees Centigrade unless otherwise stated.

EXAMPLE 1

Preparation of rac. 1-(m-methoxyphenyl)-N,N-dimethyl-2-cyclohexene-1-ethylamine hydrochloride A solution of 204 g of 2-(m-methoxyphenyl)cyclohexanone in 150 ml of dimethylformamide is added dropwise within about 30 minutes while stirring and under a nitrogen atmosphere to 57 g of sodium hydride (1.2 mol, 50% dispersion in oil) in 700 ml of absolute dimethylformamide, the temperature rising to about 40° C. The mixture is stirred for an additional hour, cooled to 10° C. and then a solution of 76 ml of chloroacetonitrile (90.6 g; 1.2 mol) in 150 ml of absolute dimethylformamide is added dropwise while stirring, the temperature is maintained at 10°–15° C. by cooling with ice water. The mixture is stirred at room temperature for an additional 2 hours, then 50 ml of ethanol are added, the mixture is poured into about 2 liters of ice water and extracted twice with 2 liters of ether each time. The ethereal phase is washed three times with 250 ml of water, dried over magnesium sulfate and evaporated. The brown oil remaining behind is chromatographed on 1 kg of silica gel. The elution is carried out firstly with about 10 liters of ether/petroleum ether (1:9) until all non-polar impurities are washed out. The 1-(m-methoxyphenyl)-2-oxo-cyclohexane-1-acetonitrile is eluted with about 15 liters of ether/petroleum ether (1:4). The fractions which are uniform in accordance with thin-layer chromatography are combined. The solvent mixture is removed by distillation, and the crystalline residue is recrystallized from dissopropyl ether to yield colorless crystals having a melting point of 62.2° C.

243 g of 1-(m-methoxyphenyl)-2-oxo-cyclohexane-1-acetonitrile are dissolved in 2.5 liters of ethanol, whereupon a total of 25 g of sodium borohydride is added portionwise while stirring. The temperature rises to about 45° C. After 1 hour, 1-(m-methoxyphenyl)-2-oxo-cyclohexane-1-acetonitrile can no longer be detected by thin-layer chromatography. After distillation of the solvent, the residue is treated with 500 ml of ice water and extracted twice with 1.5 liters of ether each time. The combined extracts are washed once in succession with 0.5 liter of water, 0.5 liter of 1 N hydrochloric acid and 0.5 liter of water, dried over magnesium sulfate, and the solvent is removed by distillation, whereby there are obtained 240 g of 1-(m-methoxyphenyl)-2-hydroxy-cyclohexane-1-acetonitrile in the form of a colorless, viscous oil which is dissolved without purification in 2 liters of pyridine and treated with 130 ml of phosphorus oxychloride. The mixture is boiled at reflux for 3 hours and subsequently evaporated in a water-jet vacuum. The residue is treated with water while cooling with ice and extracted twice with 1.5 liters of ether each time, whereupon the ethereal phases are combined, washed once in succession with 0.5 liter of water and 0.5 liter of 1 N hydrochloric acid and subsequently twice with water, dried over magnesium sulfate and evaporated. The brown oil obtained is purified on a 10-fold amount of silica gel. After elution of the impurities with about 10 liters of ether/petroleum ether (1:9), 1-(m-methoxyphenyl)-2-cyclohexene-1-acetonitrile is eluted with about 10 liters of ether/petroleum ether (1:3). The fractions which are uniform in accordance with thin-layer chromatography are combined, and the solvent is removed by distillation and the product remains behind as a light yellow oil.

454 g of the foregoing oil are dissolved in 1.5 liters of absolute tetrahydrofuran, and the solution is slowly added dropwise at room temperature under a nitrogen atmosphere to a dispersion of 152 g of lithium aluminum hydride in 1.5 liters of absolute tetrahydrofuran while stirring and with occasional cooling with ice so that the temperature does not exceed 28° C. The mixture is stirred at room temperature overnight and thereupon treated cautiously while cooling with ice and under a nitrogen atmosphere firstly with 50 ml of ethanol and then with 400 ml of tetrahydrofuran water (1:1). The precipitate obtained is removed by filtration under suction and washed well with tetrahydrofuran, whereupon the filtrate is evaporated. The viscous brown oil remaining behind is treated with 2 liters of 1 N hydrochloric acid, and the mixture is extracted three times with 0.5 liter of ether each time. The aqueous phase is made alkaline by the addition of concentrated ammonium hydroxide solution while cooling with ice, and the separated precipitate is taken up in 2 liters of ether. The ethereal solution is washed once with water, dried over magnesium sulfate and evaporated. The residue is 1-(m-methoxyphenyl)-2-cyclohexene-1-ethylamine in the form of a light brown oil which is further processed without purification.

344 g of the foregoing crude oil are treated while cooling with ice with a mixture of 380 ml of 90% formic acid and 297 ml of 35% aqueous formaldehyde solution. The mixture is stirred at 100° C. overnight, then cooled and treated with 310 ml of 20% hydrochloric acid, whereupon the mixture is evaporated to dryness. The residue is extracted three times with a mixture of 500 ml of ethanol and 500 ml of benzene, and the combined extracts are evaporated to dryness. The crude rac. 1-(m-methoxyphenyl)-N,N-dimethyl-2-cyclohexene-1-ethylamine hydrochloride is recrystallized from ethyl acetate with the addition of a small amount of ethanol, and there are obtained colorless crytstals having a melting point of 161°–162° C.

EXAMPLE 2

Preparation of rac. 1-(m-methoxyphenyl)-N,N-dimethyl-2-cyclohexene-1-propylamine By reducing 1-(m-methoxyphenyl)-2-oxo-cyclohexane-propionitrile with sodium borohydride and subsequently dehydrating the resulting 1-(m-methoxyphenyl)-2-hydroxycyclohexane-1-propionitrile with phosphorus oxychloride in pyridine in analogy to the preparation of 1-(m-methoxyphenyl)-2-cyclohexene-1-acetonitrile described in Example 1, there is obtained 1-(m-methoxyphenyl)-2-cyclohexene-1-propionitrile in the form of a pale yellowish oil.

A solution of 31.5 g of 1-(m-methoxyphenyl)-2-cyclohexene-1-propionitrile in 100 ml of absolute tetrahydrofuran is added dropwise to a suspension of 20 g of lithium aluminum hydride in 300 ml of absolute tetrahydrofuran. The mixture is subsequently boiled at reflux for 4 hours, cooled and treated firstly with 20 ml of ethanol and then with tetrahydrofuran water (1:1). The separated precipitate is removed by filtration under suction and washed well with methylene chloride, whereupon the filtrate is evaporated. The oily residue is treated with an excess of 3 N hydrochloric acid. Thereafter, the mixture is extracted with ether, the acidic-aqueous solution is made alkaline by treatment with 3 N sodium hydroxide, and the base is taken up in methylene chloride. The organic phase is dried over potassium carbonate and evaporated. The 1-(m-methoxyphenyl)-2-cyclohexene-1-propylamine remaining as the residue is processed as follows without purification. 23.0 g of the product obtained according to the preceding paragraph are treated with a mixture of 23 ml of 90% formic acid and 20 ml of 37% formaldehyde solution, and the mixture is stirred at 100° C. for 12 hours. After cooling, the mixture is made alkaline with 3 N sodium hydroxide, and the rac. 1-(m-methoxyphenyl)-N,N-dimethyl-2-cyclohexene-1-propylamine is taken up in methylene chloride. The oxalate of this compound forms colorless crystals having a melting point of 107°–109° C. (after recrystallization from ethyl acetate).

EXAMPLE 3

Preparation of rac. 1-(m-methoxyphenyl)-N-methyl-2-cyclohexene-1-ethylamine hydrochloride 45 g of 1-(m-methoxyphenyl)-2-cyclohexene-1-ethylamine are dissolved in 500 ml of ethyl formate, and the solution is boiled at reflux for 8 hours. After distillation of the excess ethyl formate, the oil obtained is taken up in ether, whereupon the organic phase is washed successively with 1 N hydrochloric acid and water, dried over magnesium sulfate and evaporated. The resulting N-[2-[1-(m-methoxyphenyl)-2-cyclohexen-1-yl]ethyl] formamide, dissolved in 200 ml of absolute tetrahydrofuran, is added dropwise to a dispersion of 24 g of lithium aluminum hydride in 250 ml of absolute tetrahydrofuran. The mixture is boiled at reflux overnight. Then it is cooled to room temperature and treated with tetrahydrofuran/water (1:1), whereupon the separated precipitate is removed by filtration under suction, and the filtrate is evaporated, and rac. 1-(m-methoxyphenyl)-N-methyl-2-cyclohexene-1-ethylamine remains as the residue. The hydrochloride of this compound melts at 177°–179° C. (colorless crystals, after recrystallization from ethyl acetate/methanol).

EXAMPLE 4

Preparation of rac. 1-(m-methoxyphenyl)-N,N-dimethyl-2-cyclohexene-1-ethylamine 5.0 g of 1-(m-methoxyphenyl)-N-methyl-2-cyclohexene-1-ethylamine are treated with a mixture of 1.5 liters of 35% aqueous formaldehyde solution and 2.0 ml of 90% formic acid, and the resulting mixture is held at 100° C. for 2 hours. After distillation of the solvent, the residue is treated with 1 N hydrochloric acid solution. The neutral portion is taken up in ether, the aqueous phase is made alkaline by the addition of 3 N sodium hydroxide and the rac. 1-(m-methoxyphenyl)-N,N-dimethyl-2-cycloexene-1-ethylamine is taken up in methylene chloride. After distillation of the solvent, the oil obtained is purified on a 10-fold amount of aluminium oxide. The fractions eluted with toluene are combined and evaporated, and pure rac. 1-(m-methoxyphenyl)-N,N-dimethyl-2-cyclohexene-1-ethylamine remains as the residue. The hydrochloride of this compound melts at 161°–162° C. (after recrystallization from ethyl acetate/ethanol).

EXAMPLE 5

Preparation of rac. 1-(m-methoxyphenyl)-N,N-dimethyl-2-cyclohexene-1-ethylamine 2.5 g of 1-(m-methoxyphenyl)-N-methyl-2-cyclohexene-1-ethylamine are dissolved in 50 ml of chloroform, this solution is treated with a solution of 1.65 g of chloral in 10 ml of chloroform, the mixture is stirred at room temperature overnight and then 1 N hydrochloric acid is added while cooling. The organic phase is washed with water until neutral, dried over magnesium sulfate and evaporated. The oily N-[2-[1-(m-methoxyphenyl)-2-cyclohexen-1-yl]ethyl]-N-methylformamide obtained is further processed as follows without purification:

A solution of 2.1 g of the foregoing oil in 50 ml of absolute tetrahydrofuran is added dropwise to a suspension of 2.0 g of lithium aluminum hydride in 20 ml of absolute tetrahydrofuran, and the mixture is boiled at reflux overnight. Then the mixture is cooled, treated with water and worked-up in the usual manner, and there is obtained rac. 1-(m-methoxyphenyl)-N,N-dimethyl-2-cyclohexene-1-ethylamine. The hydrochloride of this compound melts at 161°–162° C. (colorless crystals, after recrystallization from ethyl acetate/ethanol).

EXAMPLE 6

Preparation of rac. N-allyl-1-(m-methoxyphenyl)-N-methyl-2-cyclohexene-1-ethylamine 4.9 g of 1-(m-methoxyphenyl)-N-methyl-2-cyclohexene-1-ethylamine are dissolved in 50 ml of acetone. Thereupon, 3.5 g of potassium carbonate are added, 1.8 ml of allyl bromide are slowly added dropwise while stirring, and the mixture is stirred overnight. Subsequently, the precipitate is removed by filtration, and the filtrate is evaporated, and rac. N-allyl-1-(m-methoxyphenyl)-N-methyl-2-cyclohexene-1-ethylamine remains as the residue. The hydrochloride of this compound melts at 114°–116° C. (after recrystallization from ethyl acetate/diisopropyl ether).

EXAMPLE 7

Preparation of rac. N-cyclopropylmethyl-1-(m-methoxyphenyl)-N-methyl-2-cyclohexene-1-ethylamine hydrochloride 3.45 g of cyclopropanecarboxylic acid chloride are placed in 50 ml of methylene chloride, whereafter 5.0 g of potassium carbnate are added, and then a solution of 7.0 g of 1-(m-methoxyphenyl)-2-cyclohexene-1-ethylamine in 10 ml of methylene chloride is added dropwise while stirring. The mixture is stirred at room temperature overnight and subsequently at reflux for 30 minutes and cooled. Then, the precipitate is removed by filtration under suction, the filtrate is evaporated, and the oil obtained is taken up in ether. The ethereal solution is washed with 1 N hydrochloric acid and subsequently with water, dried over magnesium sulfate and evaporated, and N-[2-[1-(m-methoxyphenyl)-2-cyclohexen-1-yl]ethyl]-cyclopropanecarboxamide remains as the residue. 6.5 g of this compound, dissolved in 30 ml of absolute tetrahydrofuran, are added dropwise to a dispersion of 6 g of lithium aluminum hydride in 100 ml of absolute tetrahydrofuran. The mixture is boiled at reflux for 3 hours, cooled and worked-up in the usual manner, and there is obtained N-(cyclopropylmethyl)-1-(m-methoxyphenyl)-2-cyclohexene-1-ethylamine, the hydrochloride of which melts at 141°–142° C.

4.0 g of N-(cyclopropylmethyl)-1-(m-methoxyphenyl)-2-cyclohexene-1-ethylamine are treated with a mixture of 1 ml of 35% aqueous formaldehyde solution and 1.5 ml of 90% formic acid. The resulting mixture is heated at 100° for 1 hour; then 3 N hydrochloric acid is added. The solvent is removed by distillation, and the crystalline precipitate obtained is recrystallized from toluene, and there is obtained N-rac. N-cyclopropylmethyl-1-(m-methoxyphenyl)-N-methyl-2-cyclohexene-1-ethylamine hydrochloride in the form of colorless crystals having a melting point of 140°–141° C.

EXAMPLE 8

Preparation of rac. 1-(m-methoxyphenyl)-N,N-dimethyl-2-cyclohexene-1-ethylamine 10 g of 3-(m-methoxyphenyl)-2-cyclohexen-1-ol obtained by reducing 3-(m-methoxyphenyl)-2-cyclohexene-1-one with sodium borohydride, are dissolved in 100 ml of xylene, whereupon 12 g of N,N-dimethylacetamide dimethyl acetal are added, and the mixture is boiled at reflux for 8 hours. After distillation of the solvent, the oil remaining behind is chromatographed on a 30-fold amount of silica gel. The fractions which are uniform in accordance with thin-layer chromatography and which are produced by elution with methylene chloride, are combined and evaporated, and there is obtained pure 1-(m-methoxyphenyl)-N,N-dimethyl-3-cyclohexene-1-acetamide in the form of a pale yellowish oil.

A solution of 1.0 g of 1-(m-methoxyphenyl)-N,N-dimethyl-3-cyclohexene-1-acetamide in 10 ml of absolute tetrahydrofuran is added to a suspension of 1 g of lithium aluminum hydride in 50 ml of absolute tetrahydrofuran, and the mixture is boiled at reflux overnight. After the addition of water, the separated precipitate is removed by filtration under suction and washed well with tetrahydrofuran, whereupon the filtrate is evaporated. The oil remaining behind is treated with 1 N hydrochloric acid. The neutral portion is taken up in ether. The acidic phase is made alkaline by the addition of concentrated ammonia and the liberated rac. 1-(m-methoxyphenyl)-N,N-dimethyl-2-cyclohexene-1-ethylamine is taken up in methylene chloride. The hydrochloride of this compound melts at 161°–162° C. (after recrystallization from ethyl acetate/ethanol).

EXAMPLE 9

Preparation of rac. 1-(m-hydroxyphenyl)-N,N-dimethyl-2-cyclohexene-1-ethylamine 2.6 g of rac. 1-(m-methoxyphenyl)-N,N-dimethyl-2-cyclohexene-1-ethylamine, dissolved in 25 ml of chloroform, are added within 2 minutes at −50° C. while stirring to a solution of 5.8 ml of boron tribromide in 175 ml of chloroform. The mixture is stirred at −50° C. for 0.5 hour. The temperature is then allowed to rise to room temperature and thereupon the mixture is poured on to ice. The mixture is made alkaline by the addition of an excess of concentrated ammonia and is subsequently extracted with chloroform. The organic phase is washed with water, dried over magnesium sulfate and evaporated, and rac. 1-(m-hydroxyphenyl)-N,N-dimethyl-2-cyclohexene-1-ethylamine remains behind as the residue. The hydrochloride of this compound melts at 179°–181° C. (after recrystallization from methanol/ethyl acetate). The crystalline base liberated from the hydrochloride melts at 127°–129° C. (after recrystallization from methyl ethyl ketone).

EXAMPLE 10

Preparation of (+)- and (−)-(m-methoxyphenyl)-N,N-dimethyl-2-cyclohexene-1-ethylamine.

34.4 g of rac. 1-(m-methoxyphenyl)-N,N-dimethyl-2-cyclohexene-1-ethylamine are dissolved in 250 ml of absolute ethanol, and the solution is treated with a solution of 53.6 g of (+)-di-O,O'-p-toluoyl-D-tartaric acid in 250 ml of absolute ethanol. The mixture is evaporated. The residue is treated with a mixture of ethanol and benzene and again evaporated. The residue is treated with 600 ml of ethyl acetate and warmed until a clear solution results. This solution is left to stand overnight, and the separated precipitate is removed by filtration under suction. The filtrate is concentrated to 400 ml and left to stand for 6 hours, whereupon the separated precipitate is removed by filtration under suction. The combined crystallizates are recrystallized from ethanol/ether, and there is obtained (+)-[1-(m-methoxyphenyl)-N,N-dimethyl-2-cyclohexene-1-ethylamine]2,3-di-O-p-toluoyl-D-tartrate (1:1) having a melting point of 138° C.; $[\alpha]_D = +73.8°$ (c=1 in methanol).

The foregoing salt is suspended in water, and the suspension is made alkaline with an excess of 3 N sodium hydroxide. The liberated base is taken up in methylene chloride. Then the methylene chloride solution is dried over magnesium sulfate and evaporated. As the residue there is obtained (−)-1-(m-methoxyphenyl)-N,N-dimethyl-2-cyclohexene-1-ethylamine in the form of a colorless oil; $[\alpha]_D = -35.9°$ (c=1 in methanol). The hydrochloride of this compound is obtained in the form of colorless crystals having a melting point of 156°–157° C.; $[\alpha]_D = -32°$ (c=1 in methanol).

The filtrate obtained after separation of the (+)-di-toluoyl-D-tartrate is evaporated. Then the residue is treated with an excess of 3 N sodium hydroxide. The liberated base is taken up in methylene chloride, and the methylene chloride solution is evaporated. The residue is dissolved in 200 ml of absolute ethanol, whereupon a solution of 32.7 g of (−)-di-O,O'-p-toluoyl-L-tartaric acid in 250 ml of ethanol is added. The mixture is evaporated. The residue is treated with a mixture of ethanol and benzene and again evaporated. The residue obtained is dissolved in 150 ml of ethanol, and the solution is left to stand overnight. The separated crystals are removed by filtration under suction and washed with ethyl acetate, and there is obtained (+)-[1-(m-methoxyphenyl)-N,N-dimethyl-2-cyclohexene-1-ethylamine]2,3-di-O-p-toluoyl-L-tartrate (1:1) having a melting point of 138° C.; $[\alpha]_D = 73.2°$ (c=1 in methanol). The (+)-1-(m-methoxyphenyl)-N,N-dimethyl-2-cyclohexene-1-ethylamine liberated therefrom as described earlier is a colorless oil; $[\alpha]_D = +36.4°$ (c=1 in methanol). The hydrochloride of this compound melts at 156°–157° C. (from ethanol/ether); $[\alpha]_D = +31.6°$ (c=1 in methanol).

EXAMPLE 11

Preparation of rac. 1-(m-methoxyphenyl)-N,N-dimethyl-2-cyclohexene-1-ethylamine hydrochloride 200 g of ethyl 1-(m-methoxyphenyl)-2-oxo-cyclohexaneacetate are dissolved in 2000 ml of ethanol, and after treatment with 20 g of platinum oxide, the mixture is reduced with hydrogen at 50° C. and 50 bar. After separation of the catalyst, the solvent is removed by distillation, and there is obtained ethyl 2-hydroxy-1-(m-methoxyphenyl)-cyclohexaneacetate in the form of a light yellow oil.

195 g of ethyl 2-hydroxy-1-(m-methoxyphenyl)-cyclohexaneacetate are dissolved in 1800 ml of methylene chloride (dried over molecular sieve) in a 3 liter round flask provided with thermometer, stirrer and dropping funnel. The solution is treated with 93.8 g of triethylamine, and the mixture is cooled to 0° C. with an ice/methanol mixture. While stirring, there is slowly added dropwise at this temperature within about 30 minutes a solution of 78 g of methanesulfochloride in 400 ml of methylene chloride so that the temperature does not exceed 0° C. Subsequently, the mixture is stirred for 1 hour at room temperature, and the mixture is poured into 2000 ml of ice/water. The aqueous phase is extracted with 500 ml of methylene chloride. The organic phase is washed twice with 250 ml of water each time and dried over magnesium sulfate. The solvent is removed by distillation. Ethyl 1-(m-methoxyphenyl)-2-[(methylsulfonyl)oxy]cyclohexaneacetate is obtained in the form of a pale yellow oil.

100 g of ethyl 1-(m-methoxyphenyl)-2-[(methylsulfonyl)oxy]cyclohexaneacetate are dissolved in 1000 ml of hexamethylphosphoric acid triamide in a 2.5 liter sulfonation flask provided with stirrer, thermometer and reflux condenser. The solution is treated with 290 g of potassium acetate (fused and stored in a dessicator), and the mixture is stirred at 100° C. under a nitrogen atmosphere for 16 hours. After cooling, the mixture is poured into 5 liters of ice/water and extracted twice with 2 liters of ether each time. The ethereal solution is washed three times with 500 ml of water each time and dried over magnesium sulfate. The solvent is removed by distillation. There is obtained a yellow oil which, in accordance with gas chromatography, consists of ethyl 1-(m-methoxyphenyl)-2-cyclohexene-1-acetate and octahydro-3a-(m-methoxyphenyl)benzofuran-2-one. This oil is dissolved in 350 ml of ethanol. Then a solution of 15.5 g of potassium hydroxide in 155 ml of water is added, and the mixture is stirred at room temperature for 16 hours. After the addition of 100 ml of 3 N hydrochloric acid, most of the solvent is removed by distillation in a water-jet vacuum. The residue is treated with 200 ml of ice/water and 100 ml of 3 N sodium hydroxide, and the neutral portion is taken up twice in 500 ml of ether. The ethereal solution is washed twice with 50 ml of water each time. Then the combined aqueous phases are made Congo-acid by the addition of 3 N hydrochloric acid. The separated 1-(m-methoxyphenyl)-2-cyclohexene-1-acetic acid is taken up twice in 1000 ml of ether. Thereafter, the ethereal solution is washed twice with 100 ml of water each time and dried over magnesium sulfate. The solvent is removed by distillation in a water-jet vacuum, and there is obtained a yellow oil which crystallizes after treatment with 50 ml of diisopropyl ether. The separated crystals are removed by filtration under suction and dried at 30° C. The crystalline 1-(m-methoxyphenyl)-2-cyclohexene-1-acetic acid has a melting point of 59°-61° C.

38 g of 1-(m-methoxyphenyl)-2-cyclohexene-1-acetic acid are dissolved in 500 ml of methylene chloride (dried over molecular sieve). After treatment with 0.2 ml of absolute dimethylformamide, 39.5 ml of oxalyl chloride are added dropwise within about 30 minutes at 20° C. while stirring and cooling with ice. Subsequently, the mixture is stirred at room temperature for 1 hour. After distillation of the solvent, two 250 ml portions of toluene are added, and the solvent is removed by distillation in a water-jet vacuum. The crude 1-(m-methoxyphenyl)-2-cyclohexene-1-acetic acid chloride is dissolved in 400 ml of absolute ether in a 1 liter flask provided with thermometer, Claisen head and ammonia condenser. After cooling to −10° C. (dry ice/acetone), 100 ml of dimethylamine which has been condensed in a flask provided with a Claisen head and ammonia condenser are distilled into the flask containing the aforementioned ether solution of 1-(m-methoxyphenyl)-2-cyclohexene-1-acetic acid chloride. The mixture is stirred at −10° C. for 1 hour and at room temperature overnight. Thereafter, 200 ml of ice/water are added, and the mixture is shaken. The ethereal solution is washed successively with 100 ml of water, 100 ml of 1 N hydrochloric acid, 100 ml of water, 100 ml of 1 N sodium hydroxide and twice with 100 ml of water each time, dried over magnesium sulfate and evaporated, and there is obtained crude 1-(m-methoxyphenyl)-N,N-dimethyl-2-cyclohexene-1-acetamide.

10.0 g of lithium aluminum hydride are placed in 200 ml of absolute tetrahydrofuran under a nitrogen atmosphere in a 1.5 liter sulfonation flask provided with reflux condenser, thermometer, stirrer and dropping funnel, and there is added dropwise while stirring within about 1 hour a solution of 42 g of 1-(m-methoxyphenyl)-N,N-dimethyl-2-cyclohexene-1-acetamide in 450 ml of absolute tetrahydrofuran in such a manner that the temperature does not exceed 30° C. Subsequently, the mixture is stirred overnight at an oil-bath temperature of 90° C., cooled to room temperature and treated first dropwise with 50 ml of ethanol and then with tetrahydrofuran/water (1:1) until the further addition of this mixture no longer gives rise to an exothermic reaction. The mixture is then treated with 50 g of potassium carbonate, whereupon the separated precipitate is removed by filtration under suction and rinsed with methylene chloride. After distillation of the solvent, the brown oil obtained is treated with 200 ml of 1 N hydrochloric acid and extracted twice with 500 ml of ether each time. The ethereal solution is washed once with 100 ml of water. The aqueous phases are combined and made alkaline by the addition of concentrated ammonium hydroxide solution while cooling with ice. The separated base is taken up twice in 500 ml of ether each time. The organic phase is washed twice with 50 ml portions of sodium chloride solution and dried over magnesium sulfate. Thereafter, the solvent is removed by distillation. The oil obtained is chromatographed on 400 g of neutral aluminium oxide. Elution with 2500 ml of toluene gives rac. 1-(m-methoxyphenyl)-N,N-dimethyl-2-cyclohexene-1-ethylamine in the form of a colorless oil which is dissolved in 200 ml of ethanol and treated with an excess of ethanolic hydrochloric acid. After distillation of the solvent, the residue is treated twice with a mixture of 100 ml of ethanol and 100 ml of toluene. Then, the solvent is removed by distillation in a water-jet vacuum. The crystals obtained are dissolved in ethyl acetate/ethanol (20:1) at boiling temperature. After standing for 6 hours, the separated crystals are removed by filtration under suction, and there is obtained rac. 1-(m-methoxyphenyl)-N,N-dimethyl-2-cyclohexene-1-ethylamine hydrochloride in the form of colorless crystals having a melting point of 161°-162° C.

EXAMPLE 12

Preparation of rac. 1-(m-methoxyphenyl)-N,N-dimethyl-2-cyclohexene-1-ethylamine 4.6 g of hexahydro-3a-(m-methoxyphenyl)-1-methylindoline are dissolved in 100 ml of acetone, and the solution is treated with 10 ml of methyl iodide. The mixture is boiled at reflux for 10 hours. Thereafter, the solvent is removed by distillation, and the residue is recrystallized from acetone. The hexahydro-3a-(m-methoxyphenyl)-1,1-dimethyl-indolinium iodide obtained melts at 195°-196° C.

1 g of hexahydro-3a-(m-methoxyphenyl)-1,1-dimethyl-indolinium iodide is dissolved in 40 ml of water. The solution is applied to a column containing 50 g of Amberlite IRA 400 (pre-treated with sodium hydroxide; washed with distilled water until neutral). Thereafter, the column is eluted with 500 ml of distilled water. After distillation of the water, the hexahydro-3a-(m-methoxyphenyl)-1,1-dimethyl-indolinium hydroxide remaining as the residue is heated at 170° C. in a distillation apparatus in a high vacuum, an oil distilling over. This oil still contains, besides rac. 1-(m-methoxyphenyl)-N,N-dimethyl-2-cyclohexene-1-ethylamine, a relatively small amount of hexahydro-3a-(m-methoxyphenyl)-1-methylindoline.

EXAMPLE 13

Preparation of rac. 1-(m-methoxyphenyl)-N,N-dimethyl-2-cyclohexene-1-ethylamine 30 g of Amberlite IRA 400 are suspended in 100 ml of water, and the suspension is treated with a solution of 10 g of sodium fluoride in 100 ml of water. After stirring for 1 hour, the ion-exchanger is removed by filtration under suction, washed with water and placed in a chromatography column. Thereafter it is washed with water until fluoride ions can no longer be detected. A solution of 1 g of hexahydro-3a-(m-methoxyphenyl)-1,1-dimethyl-indolinium iodide in 50 ml of water is applied to the column, and it is eluted with 500 ml of water.

After distillation of the solvent, the hexahydro-3a-(m-methoxyphenyl)-1,1-dimethyl-indolinium fluoride remaining as the residue is treated five times with 100 ml of alcohol/benzene (1:1), and the solvent is removed by distillation each time. Subsequently, the residue is dried at 40° C. in a high vacuum, dissolved in 10 ml of tert.-butanol, treated with 1.46 ml of a 1.935 N sodium tert.amylate solution in toluene and stirred at room temperature for 1 hour. After distillation of the solvent, the residue is treated with water, and the product is taken up in ether. The oil obtained contains 75% of rac. 1-(m-methoxyphenyl)-N,N-dimethyl-2-cyclohexene-1-ethylamine in accordance with gas chromatography.

EXAMPLE 14

Preparation of rac.
1-(m-methoxyphenyl)-N,N-dimethyl-2-cyclohexene-1-ethylamine

The procedure described in the first paragraph of Example 13 is repeated. After distillation of the solvent, the hexahydro-3a-(m-methoxyphenyl)-1,1-dimethylindolinium fluoride remaining as the residue is dissolved in 10 ml of acetonitrile, and the solution is heated at reflux for 1 hour. After distillation of the solvent, the residue is treated with water, whereupon the base obtained is taken up in ether and distilled at 150° C. in a high vacuum. The oil obtained contains 86% of rac. 1-(m-methoxyphenyl)-N,N-dimethyl-2-cyclohexene-1-ethylamine determined by gas chromatography.

EXAMPLE 15

Preparation of rac.
1-(m-methoxyphenyl)-N,N-dimethyl-2-cyclohexene-1-ethylamine

A solution of 6.2 g of 1-(m-methoxyphenyl)-2-cyclohexene-1-acetic acid in 50 ml of absolute tetrahydrofuran is added dropwise to a suspension of 2.4 g of lithium aluminum hydride in 50 ml of absolute tetrahydrofuran, and the mixture is boiled at reflux overnight. After cooling to room temperature, the mixture is treated with 20 ml of alcohol and subsequently with 50 ml of water/tetrahydrofuran (1:1). The precipitate is removed by filtration under suction, and the filtrate is evaporated. The residue is taken up in ether, the organic phase is shaken out with 1 N sodium hydroxide and subsequently with water, dried over magnesium sulfate and evaporated. The 1-(m-methoxyphenyl)-2-cyclohexene-1-ethanol remaining as the residue is a colorless oil.

The same product is also obtained by reducing ethyl 1-(m-methoxyphenyl)-2-cyclohexene-1-acetate with lithium aluminum hydride.

1.0 g of 1-(m-methoxyphenyl)-2-cyclohexene-1-ethanol is dissolved in 10 ml of methylene chloride, and the solution is treated with 650 mg of triethylamine. While stirring and cooling to 0° C., there are added 540 mg of mesyl chloride, and the mixture is subsequently stirred at room temperature for 1 hour. The mixture is then poured into ice/water. The 2-[1-(m-methoxyphenyl)-2-cyclohexen-1-yl]ethyl methanesulfonate, a colorless oil, is taken up in ether.

1 g of 2-[1-(m-methoxyphenyl)-2-cyclohexen-1-yl]ethyl methanesulfonate is dissolved in 10 ml of isopropanol, and the solution if treated with 10 ml of freshly distilled dimethylamine. The mixture is stirred at room temperature overnight with a magnetic stirrer in a bomb tube. After evaporation of the solvent, the residue is treated with 1 N hydrochloric acid, the aqueous phase is extracted with ether and treated with concentrated ammonia, whereupon the precipitated rac. 1-(m-methoxyphenyl)-N,N-dimethyl-2-cyclohexene-1-ethylamine is taken up in methylene chloride. The hydrochloride of this compound melts at 161°–162° C.

EXAMPLE 16

Preparation of rac.
1-(m-methoxyphenyl)-N,N-dimethyl-2-cyclohexene-1-ethylamine 1.0 g of 1-(m-methoxyphenyl)-2-cyclohexene-1-ethanol is dissolved in 1 ml of toluene. After the addition of 350 mg of pyridine and 540 mg of thionyl chloride, the mixture is stirred at room temperature for 3 hours and then poured into ice/water. The 1-[1-(2-chloroethyl)-2-cyclohexen-1-yl]-3-methoxybenzene, a colorless oil, is taken up in ether.

1 g of 1-[1-(2-chloroethyl)-2-cyclohexen-1-yl]-3-methoxybenzene is dissolved in 10 ml of toluene, and the solution is treated with 10 ml of dimethylamine. The mixture is held at 150° C. for 5 hours in a bomb tube. After evaporation of the solvent, the residue is treated with 3 N hydrochloric acid. The aqueous phase is extracted with ether and made alkaline with an excess of ammonia, whereupon the precipitated rac. 1-(m-methoxyphenyl)-N,N-dimethyl-2-cyclohexene-1-ethylamine is taken up in methylene chloride. The hydrochloride of this compound melts at 161°–162° C.

EXAMPLE 17

Preparation of rac.
1-(m-methoxyphenyl)-N-methyl-2-cyclohexene-1-ethylamine

A solution of 1 ml of oxalyl chloride in 25 ml of methylene chloride is cooled to −60° C. At this temperature there is added dropwise while stirring a solution of 1.7 ml of dimethyl sulfoxide in 5 ml of methylene chloride. After 5 minutes, there is added dropwise within 5 minutes a solution of 2.32 g of 1-(m-methoxyphenyl)-2-cyclohexene-1-ethanol in 10 ml of methylene chloride. The mixture is stirred at −50° C. for 15 minutes, and after the addition of 7 ml of triethylamine, the resulting mixture is stirred at −5° C. for an additional 5 minutes. The mixture is allowed to reach room temperature, poured into ice/water, and the 1-(m-methoxyphenyl)-2-cyclohexene-1-acetaldehyde is taken up in methylene chloride. The organic phase is washed with water, dried over magnesium sulfate and evaporated. The compound obtained is a colorless oil.

1.0 g of 1-(m-methoxyphenyl)-2-cyclohexene-1-acetaldehyde is dissolved in 10 ml of methanol, and after treatment with 10 ml of methylamine, the mixture is stirred at room temperature overnight with a magnetic stirrer in a bomb tube. After evaporation of the solvent, the residue is dissolved in ethanol. Then, the solution is treated with 0.5 g of sodium borohydride, stirred at room temperature for 2 hours. The solvent is removed by evaporation, and the residue is taken up with 3 N hydrochloric acid. The aqueous phase is extracted with ether and made alkaline by the addition of concentrated ammonia, whereupon the resulting rac. 1-(m-methoxyphenyl)-N-methyl-2-cyclohexene-1-ethylamine is taken up in methylene chloride. The hydrochloride of this compound melts at 177°–179° C.

EXAMPLE A

Hard gelatin capsules:
(a) Composition:

| | |
|---|---:|
| 1-(m-Methoxyphenyl)-N,N-dimethyl-2-cyclohexene-1-ethylamine hydrochloride (active ingredient) | 100.0 mg |
| Lactose (crystalline) | 102.0 mg |
| Maize starch (white) | 45.0 mg |
| Talc | 10.4 mg |
| Magnesium stearate | 2.6 mg |
| | 260.0 mg |

(b) Manufacture:

The active ingredient is mixed with the maize starch, talc and magnesium stearate. The mixture is sieved, treated with the lactose, mixed and again sieved. The powder mixture is filled into capsules of suitable size.

We claim:

1. A compound of the formula

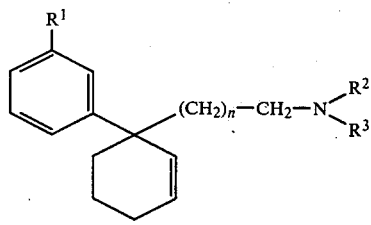

wherein $R^1$ is hydroxy or lower alkoxy, n is the integer 1 or 2, $R^2$ is lower alkyl and $R^3$ is hydrogen, lower alkyl, lower alkenyl or lower cycloalkylmethyl, or a pharmaceutically acceptable acid addition salt thereof.

2. A compound in accordance with claim 1, wherein $R^1$ is hydroxy or methoxy, $R^2$ and $R^3$ each are lower alkyl, and n is the integer 1.

3. A compound in accordance with claim 1 or claim 2, wherein each of $R^2$ and $R^3$ is methyl.

4. A compound in accordance with claim 1,1-(m-methoxyphenyl)-N,N-dimethyl-2-cyclohexene-1-ethylamine.

5. A compound in accordance with claim 1,1-(m-hydroxyphenyl)-N,N-dimethyl-2-cyclohexene-1-ethylamine.

6. A compound selected from the group consisting of 1-(m-methoxyphenyl)-N,N-dimethyl-2-cyclohexene-1-propylamine, 1-(m-methoxyphenyl)-N-methyl-2-cyclohexene-1-ethylamine, N-allyl-1-(m-methoxyphenyl-N-methyl-2-cyclohexene-1-ethylamine and N-cyclopropylmethyl-1-(m-methoxyphenyl)-N-methyl-2-cyclohexene-1-ethylamine.

7. An analgesic composition comprising an analgesically effective amount of a compound of the formula

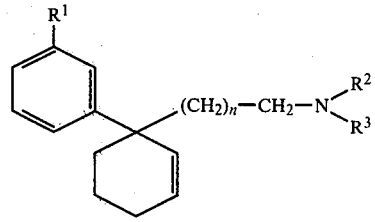

wherein $R^1$ is hydroxy or lower alkoxy, n is the integer 1 or 2, $R^2$ is lower alkyl and $R^3$ is hydrogen, lower alkyl, lower alkenyl or lower cycloalkylmethyl, or a pharmaceutically acceptable acid addition salt thereof, and an inert carrier material.

8. A method of treating pain which comprises administering an analgesically effective amount of a compound of the formula

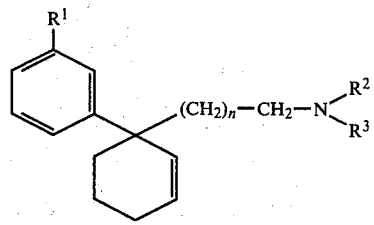

wherein $R^1$ is hydroxy or lower alkoxy, n is the integer 1 or 2, $R^2$ is lower alkyl and $R^3$ is hydrogen, lower alkyl, lower alkenyl or lower cycloalkylmethyl, or a pharmaceutically acceptable acid addition salt thereof.

9. A method in accordance with claim 8, wherein the compound is 1-(m-methoxyphenyl)-N,N-dimethyl-2-cyclohexene-1-ethylamine.

* * * * *